United States Patent [19]
Robinson et al.

[11] Patent Number: 6,114,361
[45] Date of Patent: Sep. 5, 2000

[54] 5-OXO-PYRROLIDINE-2-CARBOXYLIC ACID HYDROXAMIDE DERIVATIVES

[75] Inventors: Ralph P. Robinson, Gales Ferry; Ellen R. Laird, Mystic, both of Conn.

[73] Assignee: Pfizer Inc., New York, N.Y.

[21] Appl. No.: 09/429,937

[22] Filed: Oct. 29, 1999

Related U.S. Application Data

[60] Provisional application No. 60/107,189, Nov. 5, 1998.

[51] Int. Cl.[7] ................. A61K 31/4015; A61K 31/4439; C07D 207/12; C07D 207/16; C07D 401/04
[52] U.S. Cl. ..................... 514/340; 514/343; 514/423; 514/424; 546/278.4; 546/279.1; 548/537; 548/543; 548/550; 548/551
[58] Field of Search ....................... 514/423, 424, 514/340, 343; 548/537, 543, 550, 551; 546/278.4, 279.1

[56] References Cited

FOREIGN PATENT DOCUMENTS

WO 93/07141  4/1993  WIPO .

OTHER PUBLICATIONS

M. Zhao et al., *Tetrahedron Letters* 1998, No. 39, pp. 5323–5326, A Novel Chromium Trioxide Catalyzed Oxidation of Primary Alcohols to the Carboxylic Acids.

Hidemi Yoda et al., *Tetrahedron: Asymmetry* 1996, vol. 7, No. 7 pp. 2113–2116, An Expeditious and Practical Synthetic Process for Phytosphingosine and Tetrahydroxy–LCB from D–Glutamic Acid.

Stéphane Caron and Joel M. Hawkins, *J. Org. Chem.* 1998, 63, pp 2054–2055, Directed Ortho Metalation of Neopentyl Benzoates with LDA: Preparation of Arylboronic Acids.

A.H. Fray and A.I. Meyers, *J. Org. Chem.* 1996, 61, pp 3362–3374, Single and Double Diastereoselection in Azomethine Ylide Cycloaddition Reactions with Unsaturated Chiral Bicyclic Lactams.

*Primary Examiner*—Joseph McKane
*Assistant Examiner*—Jane C. Osweckі
*Attorney, Agent, or Firm*—Peter C. Richardson; Paul H. Ginsburg; Seth Jacobs

[57] ABSTRACT

The present invention relates to a compound of the formula

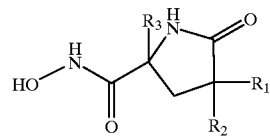

wherein $R^1$, $R^2$, $R^3$ are as defined above, to pharmaceutical compositions and methods of treatment.

19 Claims, No Drawings

5-OXO-PYRROLIDINE-2-CARBOXYLIC ACID HYDROXAMIDE DERIVATIVES

This application claims priority under 35 U.S.C. § 119 from U.S. application Ser. No. 60/107,189, filed Nov. 5, 1998, the specification of which application is hereby incorporated by reference herein.

BACKGROUND OF THE INVENTION

The present invention relates to 5-oxo-pyrrolidine-2-carboxylic acid hydroxamide derivatives, and to pharmaceutical compositions and methods of treatment.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13, an enzyme with potent activity at degrading type 11 collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date, twenty three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-α, also known as cachectin). TNF-α is recognized to be involved in many infectious and auto-immune diseases (W. Friers, *FEBS Letters*, 285, 199 (1991)). Furthermore, it has been shown that TNF-α is the prime mediator of the inflammatory response seen in sepsis and septic shock (Spooner, et al., *Clinical Immunology and Immunopathology*, 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor.

Select compounds of the invention are potent inhibitors of aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophys. Res. Comm.*, 235, 437–442, (1997)). As knowledge of the expression, physiological substrates and disease association of the ADAM's increases the full significance of the role of inhibition of this class of enzymes will be appreciated.

Diseases in which inhibition of MMP's and or ADAM's will provide therapeutic benefit include: arthritis (including osteoarthritis and rheumatoid arthritis), inflammatory bowel disease, Crohn's disease, emphysema, acute respiratory distress syndrome, asthma chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase or ADAM expression.

This invention also relates to a method of using the compounds of the invention in the treatment of the above diseases in mammals, especially humans, and to the pharmaceutical compositions useful therefore.

It is recognized that different combinations of MMP's and ADAM's are expressed in different pathological situations. As such, inhibitors with specific selectivities for individual ADAM's and/or MMP's may be preferred for individual diseases. For example, rheumatoid arthritis is an inflammatory joint disease characterized by excessive TNF levels and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

The present inventors have also discovered that it is possible to design inhibitors with differential metalloprotease activity. Specifically, for example, the inventors have been able to design molecules which selectively inhibit matrix metalloprotease-13 (MMP-13) preferentially over MMP-1.

SUMMARY OF THE INVENTION

The present invention relates to compounds of the formula

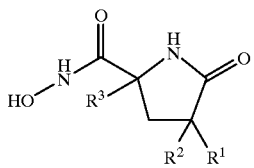

wherein $R^1$ is $(C_1-C_6)$alkyl, $(C_6-C_{10})$aryl, $(C_2-C_9)$heteroaryl, $(C_6-C_{10})$aryl$(C_1-C_6)$alkyl, $(C_6-C_{10})$aryl $(C_6-C_{10})$aryl, $(C_6-C_{10})$aryl$(C_2-C_9)$heteroayl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_{10})$heteroaryl, $(C_6-C_{10})$aryloxy $(C_1-C_6)$alkyl, $(C_6-C_{10})$aryloxy$(C_6-C_{10})$aryl, $(C_6-C_{10})$aryloxy$(C_2-C_9)$heteroaryl, $(C_2-C_9)$heteroaryloxy$(C_1-C_6)$ alkyl, $(C_2-C_9)$heteroaryloxy$(C_6-C_{10})$aryl, $(C_2-C_{10})$ heteroaryloxy$(C_2-C_9)$heteroaryl, $(C_6-C_{10})$aryl$(C_1-C_6)$alkyl $(C_6-C_{10})$aryl, $(C_6-C_{10})$aryl$(C_1-C_6)$alkyl$(C_2-C_9)$heteroaryl, $(C_6-C_{10})$aryl$(C_1-C_6)$alkoxy$(C_6-C_{10})$aryl, $(C_6-C_{10})$aryl $(C_1-C_6)$alkoxy$(C_2-C_9)$heteroaryl, $(C_6-C_{10})$aryloxy$(C_1-C_6)$ alkyl$(C_6-C_{10})$aryl, $(C_6-C_{10})$aryloxy$(C_1-C_6)$alkyl$(C_2-C_9)$ heteroaryl, $(C_2-C_9)$heteroaryl$(C_1-C_6)$alkyl$(C_6-C_{10})$aryl, $(C_2-C_{10})$heteroaryl$(C_1-C_6)$alkyl$(C_2-C_9)$heteroaryl, $(C_2-C_9)$heteroaryl$(C_1-C_6)$alkoxy$(C_6-C_{10})$aryl, $(C_2-C_9)$ heteroaryl$(C_1-C_6)$alkoxy$(C_2-C_9)$heteroaryl, $(C_2-C_9)$ heteroaryloxy$(C_1-C_6)$alkyl$(C_6-C_{10})$aryl, $(C_2-C_9)$ heteroaryloxy$(C_1-C_6)$alkyl$(C_2-C_9)$heteroaryl, $(C_6-C_{10})$aryl $(C_6-C_{10})$aryl$(C_1-C_6)$alkyl or $(C_6-C_{10})$aryl$(C_1-C_6)$alkoxy $(C_1-C_6)$alkyl, wherein each of said $(C_6-C_{10})$aryl or $(C_2-C_9)$ heteroaryl moieties is optionally substituted on any of the ring carbon atoms capable of forming an additional bond by one or more substituents per ring, independently selected from fluoro, chloro, bromo, $(C_1-C_6)$alkyl, $(C_1-C_6)$alkoxy, perfluoro$(C_1C_3)$alkyl, perfluoro$(C_1-C_3)$alkoxy and $(C_6-C_{10}o)$aryloxy; and $R^2$ and $R^3$ are independently selected from H, $(C_1-C_6)$ alkyl, and $CH_2(C_6-C_{10})$aryl;

and the pharmaceutically acceptable salts thereof.

Preferred compounds of the present invention relate to compounds wherein $R^1$ is $(C_6-C_{10})$aryl, $(C_6-C_{10})$aryloxy $(C_6-C_{10}l)$aryl, $(C_6-C_{10})$aryl$(C_6-C_{10})$aryl, $(C_6-C_{10})$aryloxy $(C_2-C_9)$heteroaryl, $(C_2-C_9)$heteroaryl, $(C_2-C_9)$heteroaryl $(C_2-C_9)$heteroaryl, $(C_6-C_{10})$aryl$(C_1-C_6)$alkoxy$(C_6-C_{10})$ aryl, $(C_2-C_9)$heteroaryloxy$(C_6-C_{10})$aryl, $(C_6-C_{10})$aryl $(C_1-C_6)$alkoxy$(C_2-C_9)$heteroaryl, $(C_2-C_9)$heteroaryloxy $(C_2-C_9)$heteroaryl, $(C_6-C_{10})$aryl$(C_2-C_9)$heteroaryl, $(C_2-C_9)$heteroaryl$(C_6-C_{10})$aryl, $(C_2-C_9)$heteroaryl$(C_1-C_6)$ alkoxy$(C_6-C_{10})$aryl, or $(C_2-C_9)$heteroaryl$(C_1-C_6)$alkoxy $(C_2-C_9)$heteroaryl, wherein each $(C_6-C_{10})$aryl or $(C_2-C_9)$ heteroaryl moieties of said $(C_6-C_{10})$aryl, $(C_6-C_{10})$aryloxy $(C_6-C_{10})$aryl, $(C_6-C_{10})$aryl$(C_6-C_{10})$aryl, $(C_6-C_{10})$aryloxy $(C_2-C_9)$heteroaryl, $(C_2-C_9)$heteroaryl, $(C_6-C_{10})$aryl $(C_1-C_6)$alkoxy$(C_6-C_{10})$aryl, $(C_2-C_9)$heteroaryloxy $(C_6-C_{10})$aryl, $(C_6-C_{10})$aryl$(C_1-C_6)$alkoxy$(C_2-C_9)$ heteroaryl, $(C_2-C_9)$heteroaryloxy$(C_2-C_9)$heteroaryl, $(C_6-C_{10})$aryl$(C_2-C_9)$heteroaryl, $(C_2-C_9)$heteroaryl$(C_6-C_{10})$ aryl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl is optionally substituted on any of the ring carbon atoms capable of forming an additional bond by one or more substituents per ring (preferably one to three substituents, most preferably 0–2 substituents) independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy.

In another embodiment, $R^2$ and $R^3$ are hydrogen. In a further embodiment, one or both of $R^2$ and $R^3$ are independently selected from $(C_1-C_6)$alkyl, and $CH_2(C_6-C_{10})$aryl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, bromo, perfluoro$(C_1-C_6)$alkyl (including trifluoromethyl), $(C_1-C_6)$alkoxy, $(C_6-C_{10})$aryloxy, perfluoro$(C_1-C_3)$alkoxy (including trifluoromethoxy and difluoromethoxy) and $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl. Preferred heteroaryls include pyridyl, furyl, thienyl, isothiazolyl, pyrazinyl, pyrimidyl, pyrazolyl, isoxazolyl, thiazolyl or oxazolyl. Most preferred heteroaryls include pyridyl, furyl or thienyl.

The compound of formula I may have chiral centers and therefore exist in different enantiomeric forms. This invention relates to all optical isomers, tautomers and stereoisomers of the compounds of formula I and mixtures thereof.

More preferred compounds of the present invention relate to a compound of formula I with the stereochemistry

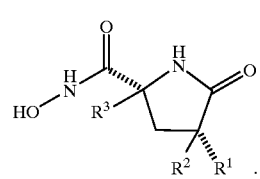

More preferred compounds of the present invention relate to a compound of formula 1, wherein $R^1$ is optionally substituted $(C_6-C_{10})$aryl, $(C_6-C_{10})$aryloxy$(C_6-C_{10})$aryl, $(C_2-C_9)$heteroaryloxy$(C_6-C_{10})$aryl, $(C_6-C_{10})$aryl$(C_1-C_6)$ alkoxy$(C_6-C_{10})$aryl, preferably substituted with one to three substituents (most preferably zero or one substituent) independently selected from hydrogen, fluoro, chloro, $(C_1-C_6)$ alkyl or $(C_1-C_6)$alkoxy. When the compound of formula I possesses a substituent, that substituent is most preferably in the para or ortho position of the terminal ring.

Specific preferred compounds of formula I are selected from the group consisting of:

(2R, 4S)-4-(4-methoxyphenyl)-5-oxopyrrolidine-2-carboxylic acid hydroxyamide, and (2R, 4S)-4-[4-(4-fluorophenoxy)phenyl]-5-oxo-pyrrolidine-2-carboxylic acid hydroxyamide.

Other compounds of formula I are selected from the group consisting of:

(2R, 4S)-5-oxo-4-(4-phenoxyphenyl)-pyrrolidine-2-carboxylic acid hydroxyamide, (2R, 4S)-4-[4-(4-chlorophenoxy)phenyl]-5-oxopyrrolidine-2-carboxylic acid hydroxyamide, (2R, 4S)-4-[3-(4-chlorophenoxy)phenyl]-5-oxopyrrolidine-2-carboxylic acid hydroxyamide, (2R, 4S)-4-[3-(4-fluorophenoxy)phenyl]-5-oxopyrrolidine-2-carboxylic acid hydroxyamide, (2R, 4S)-5-oxo-4-[4-(pyridin-4-yloxy)-phenyl]pyrrolidine-2-carboxylic acid hydroxyamide, (2R, 4S)-4-biphenyl-4-yl-5-oxo-pyrrolidine-2-carboxylic acid hydroxyamide, (2R, 4S)-4-(4'-fluorobiphenyl-4-yl)-5-oxopyrrolidine-2-carboxylic acid hydroxyamide, (2R, 4S)-4-(4-benzyloxyphenyl)-5-oxopyrrolidine-2-carboxylic acid hydroxyamide, (2S, 4S )-5-oxo-4-(4-phenethylphenyl)-pyrrolidine-2-carboxylic acid hydroxyamide, (2R, 4S)-4-[4-(4-fluorobenzyloxy)phenyl]-5-oxopyrrolidine-2-carboxylic acid hydroxyamide, (2R, 4S)-4-[4-(3,5-difluorobenzyloxy)phenyl]-5-oxopyrrolidine-2-carboxylic acid hydroxyamide, (2R, 4S)4-(4-methoxybenzyl)-5-oxopyrrolidine-2-carboxylic acid hydroxyamide, (2R, 4S)-4-(4'-fluorobiphenyl-4-ylmethyl)-5-oxopyrrolidine-2-carboxylic acid hydroxyamide, (2R, 4S )-4-naphthalen-2-yl-5-oxo-pyrrolidine-2-carboxylic acid hydroxyamide, (2R, 4S)-4-[4-(4-fluorophenoxy)-phenyl]-2,4-dimethyl-5-oxo-pyrrolidine-2-carboxylic acid hydroxyamide, (2R, 4S)-4-[4-(4-fluorophenoxy)-phenyl]-4-methyl-5-oxo-pyrrolidine-2-carboxylic acid hydroxyamide, (2R, 4R)-4-benzyl-5-oxo-4-(4-phenoxyphenyl)-pyrrolidine-2-carboxylic acid hydroxyamide, (2R, 4S)-4-[4-(4-chlorophenoxy)phenyl]-4-methyl-5-oxo-pyrrolidine-2-carboxylic acid hydroxyamide, and (2R, 4S)-4-[4-(4-chlorophenoxy)phenyl]-2,4-dimethyl-5-oxo-pyrrolidine-2-carboxylic acid hydroxyamide.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The present invention also relates to a pharmaceutical composition for the treatment of a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase activity and other diseases characterized by mammalian reprolysin activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase activity and other diseases characterized by mammalian reprolysin activity in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably ADAM-17) in a mammal, including a human, comprising administering to said mammal an effective amount of a compound of formula I or a pharmaceutically acceptable salt thereof.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, miratex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as Aricept, tacrine, COX-2 inhibitors, propentofylline or metryfonate.

The compounds of the present invention may also be used in combination with osteoporosis agents such as droloxifene or fosomax and immunosuppressant agents such as FK-506 and rapamycin.

DETAILED DESCRIPTION OF THE INVENTION

The following reaction schemes illustrate the preparation of the compounds of the present invention. Unless otherwise indicated, $R^1$, $R^2$, and $R^3$ in the reaction schemes and the discussion that follows are defined as above.

Reaction scheme 1 shows the synthesis of compounds where $R^2$ is hydrogen, $(C_1-C_6)$ alkyl or $CH_2(C_6-C_{10})$aryl and $R^3$ is hydrogen.

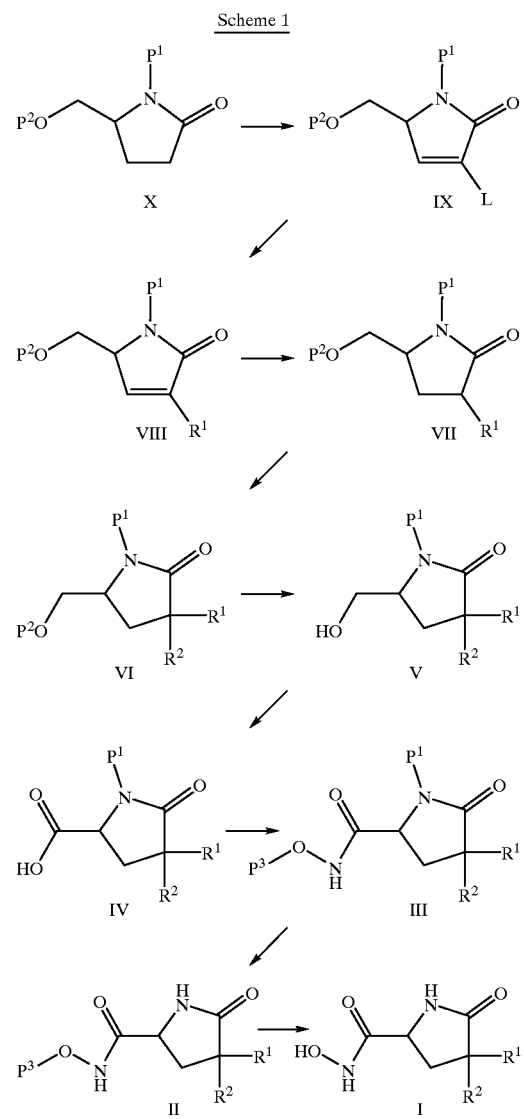

Referring to Scheme 1, compounds of the formula I are prepared from hydroxamic acid derivatives of the formula II by removal of the hydroxy amide protecting group $P^3$. When $P^3$ is benzyl, removal of the hydroxy amide protecting group is carried out by hydrogenolysis using catalytic palladium on barium sulfate in a polar solvent at a temperature from about 20° C. to about 25° C., i.e. room temperature, for a period of about 1 hour to about 5 hours, preferably about 3 hours. When $P^3$ is other than benzyl, removal is facilitated such as described in Greene and Wuts, "Protective Groups in Organic Synthesis" (Willey Interscience, 2nd Ed.) (1991), Chapter 2.

The compound of formula II is prepared from a compound of formula III by removal of the $P^1$ protecting group, wherein $P^1$ is as defined below. When $P^1$ is a t-butoxy carbonyl protecting group, removal is effected by using an acid in an inert solvent. When $P^1$ is other than t-butoxy carbonyl, removal is as described in Greene and Wuts, id. at p. 397–405. Suitable acids include hydrochloric and trifluoroacetic acid, preferably hydrochloric acid. Suitable solvents include methylene chloride, diethyl ether, or chloroform, preferably methylene chloride. The reaction is carried out at a temperature ranging from about −25° C. to 50° C.; preferably the temperature may range from about 20° C. to about 25° C. (i.e. room temperature). The reaction is conducted over a period of about 15 minutes to about 2 hours, preferably about 30 minutes.

The hydroxamic acid derivative of formula III is prepared from a carboxylic acid compound of formula IV by reaction with a suitably protected hydroxylamine derivative of the formula $P^3\text{-ONH}_2$, wherein $P^3$ is as defined in Greene and Wuts, id., and (benzotriazol-1-yloxy)tris(dimethylamino) phosphonium hexafluorophosphate in the presence of a base, at room temperature, in a polar solvent. Suitable bases include triethylamine, N-methylmorpholine or diisopropylethylamine, preferably diisopropylethylamine. Suitable solvents include THF, methylene chloride, N,N-dimethylformamide or N-methylpyrrolidin-2-one, preferably methylene chloride. Specific $P^3$ protecting groups include benzyl, t-butyidimethylsilyl, trimethylsilyl, 2-(trimethylsilyl)ethyl or allyl. The aforesaid reaction is conducted for a period of about 2 hours to about 24 hours, preferably about 16 hours. The temperature of the aforesaid reaction varies from about 0° C. to about 60° C., preferably about 20° C. to about 25° C. (room temperature).

The carboxylic acid of formula IV is prepared by oxidation of an alcohol of formula V in the presence of periodic acid and catalytic chromium trioxide, in a polar solvent. Suitable solvents include acetonitrile or water, preferably wet acetonitrile (0.75 volume percent water). Suitable temperatures for the aforesaid reaction range from about −10° C. to about 25° C., preferably the temperature is about 0° C. The reaction is complete within about 10 minutes to about 24 hours, preferably about 0.5 hours. Alternative oxidation conditions are described in Zhao, et al., Tet. Lett., 39, 5323–5326 (1998).

The alcohol of formula V is prepared from a compound of formula VI by removal of the protecting groups at $P^2$, wherein $P^2$ is as defined below. When $P^2$ is tert-butyl dimethylsilyl, the reaction is performed by mild hydrolysis in the presence of dilute aqueous mineral acid and a solvent such as diethyl ether. Suitable aqueous mineral acids include dilute hydrochloric acid or sulfuric acid, preferably 0.5 molar hydrochloric acid. The reaction is carried out at a temperature ranging from about 0° C. to 50° C.; preferably the temperature may range from about 20° C. to about 25° C. (i.e. room temperature). The reaction is conducted over a period of about 2 hours to about 48 hours, preferably about 16 hours.

The compound of formula VI, where $R^2$ is $(C_1-C_6)$ alkyl or $CH_2(C_6-C_{10})$aryl, is prepared from a compound of formula VII by reacting VII with an alkylating agent of the formula $R^2\text{-Z}$, where Z is bromo or iodo, and strong base such as lithium diisopropylamide or lithium (bis) trimethylsilylamide (preferably lithium diisopropylamide) in an inert solvent such as diethyl ether or tetrahydrofuran (preferably tetrahydrofuran). The reaction is carried out at a temperature of from −78° C. to 0C, preferably −78° C. for a period of from 1 to 24 hours, preferably about 16 hours.

The compound of formula VII is prepared from a compound of formula VII by hydrogenation under an atmosphere of hydrogen in the presence of a catalyst in a reaction inert solvent. Suitable catalysts include palladium on barium sulfate, palladium on carbon, palladium hydroxide on carbon or carbon black. The preferred catalyst is palladium hydroxide on carbon. Suitable solvents include an alcohol such as ethanol, methanol or isopropanol, preferably methanol. The aforesaid reaction may be performed at a pressure from about 1 to about 5 atmospheres, preferably about 3 atmospheres. Suitable temperatures for the aforesaid reaction range from about 20° C. (room temperature) to about 60° C., preferably the temperature may range from about 20° C. to about 25° C. (i.e. room temperature). The reaction is complete within about 0.5 hours to about 5 hours, preferably about 3 hours. Alternatively, the reduction can be performed using dissolving metal conditions or by using L-selectride.

The compound of formula VIII can be prepared from a compound of the formula IX by Suzuki coupling, preferably by reaction with a boronic acid of the formula

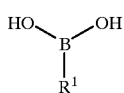

in the presence of a catalyst and a base in a suitable solvent. Suitable catalysts include palladium (II) acetate, tetrakis (triphenylphosphene)palladium and tetrakis[tris-(2-methoxyphenyl)-phosphine]palladium, preferably tetrakis (triphenylphosphene)palladium. Suitable bases include aqueous sodium carbonate, aqueous potassium carbonate, or aqueous cesium carbonate, preferably aqueous sodium carbonate. Suitable solvents include ethers, toluene, and hexane, preferably toluene. Suitable temperatures for the aforesaid reaction range from about 20° C. (room temperature) to about 110° C., preferably the temperature may range from about 75° C. to about 110C. The reaction is complete within about 0.5 hours to about 24 hours, preferably about 16 hours. Suzuki couplings are well known to those of ordinary skill in the art such as described in Suzuki, Pure Appl. Chem., 63, 419–422 (1991), Tetrahedron, 263 (1997) and Chem. Rev., 95, 2457–2483 (1995). Boronic acids can also be prepared by methods well known to those of ordinary skill in the art, such as those described in Caron, et al., JOC, 63, 2054–2055 (1998).

Compounds of the formula VII can also be prepared from compounds of the formula IX by reaction with organometallic reagents of the formula $R^1\text{-M}$, wherein M is magnesium, lithium, tin, zinc, copper, or boron, in the presence of an appropriate transition metal catalyst such as catalysts based on palladium or nickel.

The compound of formula IX, wherein L is bromo or iodo, can be prepared from a compound of formula X by reaction with a base, phenylselenenylbromide and a halogenating agent followed by oxidation in the presence of hydrogen peroxide. Suitable bases include lithium bis (trimethylsilyl)amide or lithium diisopropylamide, preferably lithium bis(trimethylsilyl)amide. Suitable halogenating agents include 1,2-dibromotetrachloroethane or N-iodosuccinamide, preferably 1,2-dibromotetrachloroethane. Suitable temperatures for the aforesaid reaction range from about −78° C. to about −30° C., preferably the temperature is about −78° C. The reaction is complete within about 0.5 hours to about 5 hours, preferably about 3 hours. The oxidation step is performed at a temperature of about 0° C. to about 50° C., preferably at about room temperature. The aforesaid oxidation step is complete within about 2 hours to about 24 hours, preferably about 16 hours. Suitable solvents for the oxidation step include methylene chloride. Other conditions for the aforesaid reaction are described in Fray, et al., *JOC*, 61, 3362–3374 (1996).

Compounds of the formula X, wherein $P^1$ and $P^2$ are protective groups as described in Greene and Wuts, supra, are known or can be made by methods well known to those of ordinary skill in the art. One example of a method of preparation of a compound of formula X, wherein $P^1$ is tertbutoxy carbonyl and $P^2$ is t-butyldimethylsilyl, is described in Yoda et al., *Tetrahedron*, 7(7), 2113–2116 (1996). Suitable $P^1$ protecting groups include tert-butoxycarbonyl, benzyloxycarbonyl, methoxycarbonyl, 2-(trimethylsilyl)ethyloxycarbonyl, trifluoroacetyl or 2,2,2-trichloroethoxycarbonyl. Suitable $P^2$ protecting groups include t-butyldiphenylsilyl, benzyl, methoxymethyl (MOM) or tetrahydropyranyl.

Scheme 2 shows the synthesis of compounds where $R^2$ is hydrogen and $R^3$ is $(C_1–C_6)$ alkyl or $CH_2(C_6–C_{10})$aryl.

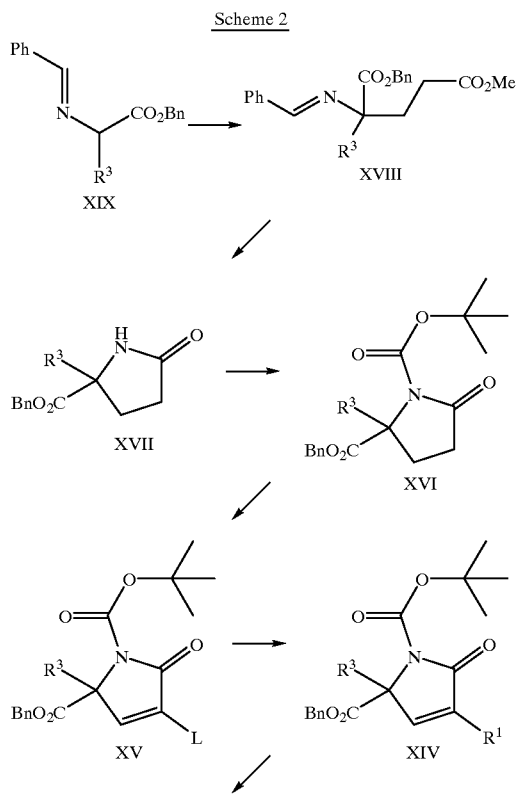

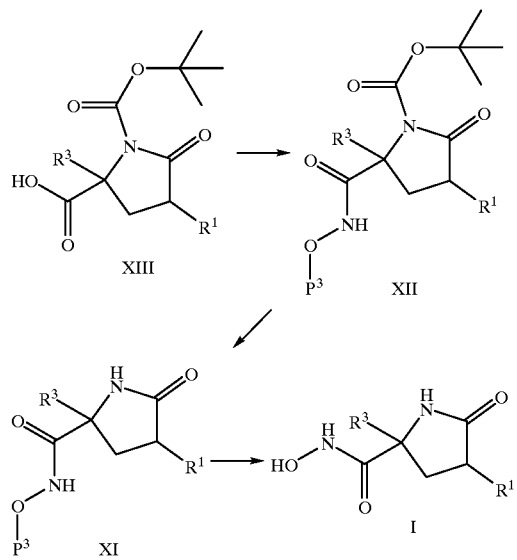

Referring to Scheme 2, compounds of the formula I are prepared from hydroxamic acid derivatives of the formula XI by removal of the hydroxy amide protecting group $P^3$. When $P^3$ is benzyl, removal of the hydroxy amide protecting group is carried out by hydrogenolysis using catalytic palladium on barium sulfate in a polar solvent at a temperature from about 20° C. to about 25° C., i.e. room temperature, for a period of about 1 hour to about 5 hours, preferably about 3 hours. When $P^3$ is other than benzyl, removal is facilitated such as described in Greene and Wuts, supra.

The compound of formula XI is prepared from a compound of formula XII by treatment with an acid in an inert solvent. Suitable acids include hydrochloric and trifluoroacetic acid, preferably hydrochloric acid. Suitable solvents include methylene chloride, diethyl ether, or chloroform, preferably methylene chloride. The reaction is carried out at a temperature ranging from about −25° C. to 50° C.; preferably the temperature may range from about 20° C. to about 25° C. (i.e. room temperature). The reaction is conducted over a period of about 15 minutes to about 2 hours, preferably about 30 minutes.

The hydroxamic acid derivative of formula XII is prepared from a carboxylic acid compound of formula XII by reaction with a suitably protected hydroxylamine derivative of the formula $P^3$-$ONH_2$, wherein $P^3$ is as defined in Greene and Wuts, id., and (benzotriazol-1-yloxy)tris (dimethylamino) phosphonium hexafluorophosphate in the presence of a base, at room temperature, in a polar solvent. Suitable bases include triethylamine, N-methylmorpholine or diisopropylethylamine, preferably diisopropylethylamine. Suitable solvents include THF, methylene chloride, N,N-dimethylformamide or N-methylpyrrolidin-2-one, preferably methylene chloride. Specific $P^3$ protecting groups include benzyl, t-butyidimethylsilyl, trimethylsilyl, 2-(trimethylsilyl)ethyl or allyl. The aforesaid reaction is conducted for a period of about 2 hours to about 24 hours, preferably about 16 hours. The temperature of the aforesaid reaction varies from about 0° C. to about 60° C., preferably about 20° C. to about 25° C. (room temperature).

Compounds of formula XII are prepared from compounds of formula XIV by hydrogenation under an atmosphere of hydrogen in the presence of a catalyst in a reaction inert solvent. Suitable catalysts include palladium on barium sulfate, palladium on carbon, palladium hydroxide on carbon or carbon black. The preferred catalyst is palladium hydroxide on carbon. Suitable solvents include an alcohol such as ethanol, methanol or isopropanol, preferably methanol. The aforesaid reaction may be performed at a pressure from about 1 to about 5 atmospheres, preferably about 3 atmospheres. Suitable temperatures for the aforesaid reaction range from about 20° C. (room temperature) to about 60° C., preferably the temperature may range from about 20° C. to about 25° C. (i.e. room temperature). The reaction is complete within about 0.5 hours to about 5 hours, preferably about 3 hours. Alternatively, the reduction can be performed using dissolving metal conditions.

The compound of formula XIV can be prepared from a compound of the formula XV by Suzuki coupling, preferably by reaction with a boronic acid of the formula

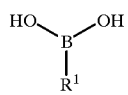

in the presence of a catalyst and a base in a suitable solvent. Suitable catalysts include palladium (II) acetate, tetrakis(triphenylphosphene)palladium and tetrakis[tris-(2-methoxyphenyl)-phosphine]palladium, preferably tetrakis(triphenylphosphene)palladium. Suitable bases include aqueous sodium carbonate, aqueous potassium carbonate, or aqueous cesium carbonate, preferably aqueous sodium carbonate. Suitable solvents include ethers, toluene, and hexane, preferably toluene. Suitable temperatures for the aforesaid reaction range from about 20° C. (room temperature) to about 110° C., preferably the temperature may range from about 75° C. to about 110° C. The reaction is complete within about 0.5 hours to about 24 hours, preferably about 16 hours.

Compounds of the formula XIV can also be prepared from compounds of the formula XV by reaction with organometallic reagents of the formula $R^1$-M, wherein M is magnesium, lithium, tin, zinc, copper, or boron, in the presence of an appropriate transition metal catalyst such as catalysts based on palladium or nickel.

The compounds of formula XV, wherein L is bromo or iodo, can be prepared from compounds of formula XVI by reaction with a base, phenylselenenylbromide and a halogenating agent followed by oxidation in the presence of hydrogen peroxide. Suitable bases include lithium bis(trimethylsilyl)amide or lithium diisopropylamide, preferably lithium bis(trimethylsilyl)amide. Suitable halogenating agents include 1,2-dibromotetrachloroethane or N-iodosuccinamide, preferably 1,2-dibromotetrachloroethane. Suitable temperatures for the aforesaid reaction range from about −78° C. to about −30° C., preferably the temperature is about −78° C. The reaction is complete within about 0.5 hours to about 5 hours, preferably about 3 hours. The oxidation step is performed at a temperature of about 0° C. to about 50° C., preferably at about room temperature. The aforesaid oxidation step is complete within about 2 hours to about 24 hours, preferably about 16 hours. Suitable solvents for the oxidation step include methylene chloride. Other conditions for the aforesaid reaction are described in Fray, et al., supra.

The compounds of XVI are prepared from compounds of formula XVII by reacting compounds of formula XVII with di-tert-butyl dicarbonate in the presence of a base such as triethylamine or diisopropylethylamine, preferably triethylamine, and a catalytic amount of 4-dimethylaminopyridine in an inert solvent such as methylene chloride, chloroform or tetrahydrofuran, preferably tetrahydrofuran. The reaction is carried out at a temperature of from 0° C. to 50° C., preferably about 25° C., for 1 to 48 hours, preferably about 16 hours.

The compounds of formula XVII are prepared from compounds of formula XVIII by heating the compounds of formula XVIII in water or in a mixture of tetrahydrofuran, methanol and water, constituted such that XVIII is soluble. This reaction is carried out at a temperature of 50° C. to 180° C. for a period of 1 to 48 hours, preferably about 16 hours.

The compounds of formula XVIII are prepared from the compounds of XIX by reacting the amino acid derivative of formula XIX with methyl acrylate and a base such as potassium carbonate, cesium carbonate or cesium hydroxide hydrate, preferably potassium carbonate, in the presence of benzyl triethylammonium chloride in a solvent such as acetonitrile or methylene chloride, preferably acetonitrile. The reaction is carried out at a temperature of from 0° C. to 50° C., preferably about 25° C. for 1 to 24 hours, preferably about 2 hours.

Compounds of the formula XIX are known or can be made by methods well known to those of ordinary skill in the art.

Scheme 3 shows the synthesis of compounds of the invention where $R^2$ and $R^3$ are independently $(C_1–C_6)$ alkyl or $CH_2(C_6–C_{10})$aryl.

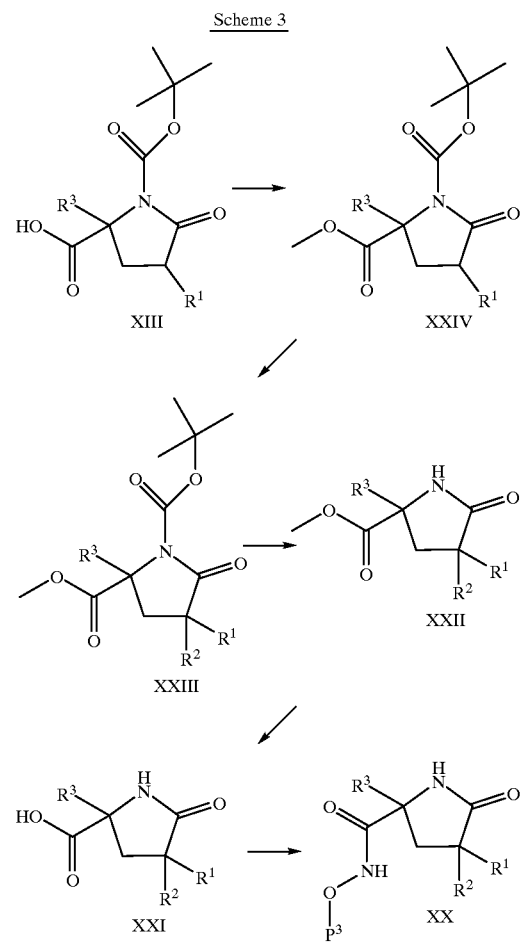

Scheme 3

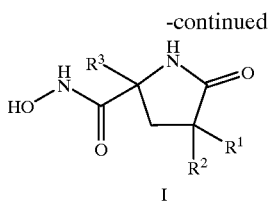

I

Referring to Scheme 3, compounds of the formula I are prepared from hydroxamic acid derivatives of the formula XX by removal of the hydroxy amide protecting group $P^3$. When $P^3$ is benzyl, removal of the hydroxy amide protecting group is carried out by hydrogenolysis using catalytic palladium on barium sulfate in a polar solvent at a temperature from about 20° C. to about 25° C., i.e. room temperature, for a period of about 1 hour to about 5 hours, preferably about 3 hours. When $P^3$ is other than benzyl, removal is facilitated such as described in Greene and Wuts, supra.

The hydroxamic acid derivatives of formula XX are prepared from carboxylic acid compounds of formula XXI by reaction with a suitably protected hydroxylamine derivative of the formula $P^3$-$ONH_2$, wherein $P^3$ is as defined in Greene and Wuts, id., and (benzotriazol-1-yloxy)tris (dimethylamino) phosphonium hexafluorophosphate in the presence of a base, at room temperature, in a polar solvent. Suitable bases include triethylamine, N-methylmorpholine or diisopropylethylamine, preferably diisopropylethylamine. Suitable solvents include THF, methylene chloride, N,N-dimethylformamide or N-methylpyrrolidin-2-one, preferably methylene chloride. Specific $P^3$ protecting groups include benzyl, t-butyldimethylsilyl, trimethylsilyl, 2-(trimethylsilyl)ethyl or allyl. The aforesaid reaction is conducted for a period of about 2 hours to about 24 hours, preferably about 16 hours. The temperature of the aforesaid reaction varies from about 0° C. to about 60° C., preferably about 20° C. to about 25° C. (room temperature).

The compounds of formula XXI are prepared from compounds of formula XXII by reacting compounds of formula XXII with a base such as lithium hydroxide, sodium hydroxide or potassium hydroxide, preferably lithium hydroxide, in a mixture of water, methanol and tetrahydrofuran (constituted such that XXII is soluble). The reaction is carried out at a reaction temperature of 20° C. to 60° C., preferably about 25° C. for 1 to 48 hours, preferably about 2 hours.

Compounds of formula XXII are prepared from compounds of formula XXIII by treatment with an acid in an inert solvent. Suitable acids include hydrochloric and trifluoroacetic acid, preferably hydrochloric acid. Suitable solvents include methylene chloride, diethyl ether, or chloroform, preferably methylene chloride. The reaction is carried out at a temperature ranging from about −25° C. to 50° C.; preferably the temperature may range from about 20° C. to about 25° C. (i.e. room temperature). The reaction is conducted over a period of about 15 minutes to about 2 hours, preferably about 30 minutes.

Compounds of the formula XXIII are prepared from compounds of formula XXIV by reacting XXIV with an alkylating agent of the formula $R^2$-Z, where Z is bromo or iodo, and strong base such as lithium diisopropylamide or lithium (bis)trimethylsilylamide (preferably lithium diisopropylamide) in an inert solvent such as diethyl ether or tetrahydrofuran (preferably tetrahydrofuran). The reaction is carried out at a temperature of from −78° C. to 0° C., preferably −78° C. for a period of from 1 to 24 hours, preferably about 16 hours.

Compounds of formula XXIV are prepared from compounds of formula XIII by reacting compounds of formula XII with methyl iodide and a base such as sodium carbonate, potassium carbonate or cesium carbonate, preferably cesium carbonate, in an inert solvent such as dimethylformamide or acetone, preferably dimethylformamide. The reaction is conducted at a temperature of 0° C. to 50° C., preferably about 25° C. Reaction time: 1 to 48 hours, preferably about 16 hours.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula 1. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the production of tumor necrosis factor is shown by the following in vitro assay tests.

Biological Assay

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 ml is then added to appropriate wells of the microfluor plate. Final concentration of collagenase in the assay is 60 ng/ml.

Substrate (DNP-Pro-Cha-Gly-Cys(Me)-His-Ala-Lys(NMA)-NH$_2$) is made as a 5 mM stock in dimethylsulfoxide and then diluted to 20 μM in assay buffer. The assay is initiated by the addition of 50 ml substrate per well of the microfluor plate to give a final concentration of 10 mM.

Fluorescence readings (360 nM excitation, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration versus % control (inhibitor fluorescence divided by fluorescence of collagenase alone ×100). IC$_{50}$'s are determined from the concentration of inhibitor that gives a signal that is 50% of the control.

If IC$_{50}$'s are reported to be less than 0.03 mM then the inhibitors are assayed at concentrations of 0.3 mM, 0.03 mM, and 0.003 mM.

Inhibition of Gelatinase (MMP-2)

Human recombinant 72 kD gelatinase (MMP-2, gelatinase A) is activated for 16–18 hours with 1mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM CaCl$_2$, 20 μM ZnCl$_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-NH$_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. IC$_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM CaCl$_2$ and 0.05% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 200 ng/mL in assay buffer, 25 μL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-NH$_2$) is diluted in assay buffer to 6 μM. The assay is initiated by addition of 50 μL of diluted substrate yielding a final assay concentration of 3 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control ×100). Data is plotted as inhibitor concentration versus percent of enzyme control. $IC_{50}$'s are defined as the concentration of inhibitor that gives a signal that is 50% of the positive enzyme control.

Inhibition of MMP-13

Human recombinant MMP-13 is activated with 2mM APMA (p-aminophenyl mercuric acetate) for 2.0 hours, at 37° C. and is diluted to 240 ng/ml in assay buffer (50 mM Tris, pH 7.5, 200 mM sodium chloride, 5mM calcium chloride, 20 mM zinc chloride, 0.02% brij 35). Twenty-five microliters of diluted enzyme is added per well of a 96 well microfluor plate. The enzyme is then diluted in a 1:4 ratio in the assay by the addition of inhibitor and substrate to give a final concentration in the assay of 60 ng/ml.

Stock solutions (10 mM) of inhibitors are made up in dimethylsulfoxide and then diluted in assay buffer as per the inhibitor dilution scheme for inhibition of human collagenase-1 (MMP-1): Twenty-five microliters of each concentration is added in triplicate to the microfluor plate. The final concentrations in the assay are 30 mM, 3mmM, 0.3 mmM, and 0.03 mmM.

Substrate (Dnp-Pro-Cha-Gly-Cys(Me)-His-Ala-Lys (NMA)-NH$_2$) is prepared as for inhibition of human collagenase (MMP-1) and 50 μl is added to each well to give a final assay concentration of 10 μM. Fluorescence readings (360 nM excitation; 450 nM emission) are taken at time 0 and every 5 minutes for 1 hour.

Positive controls and negative controls are set up in triplicate as outlined in the MMP-1 assay.

$IC_{50}$'s are determined as per inhibition of human collagenase (MMP-1). If $IC_{50}$'s are reported to be less than 0.03 mM, inhibitors are then assayed at final concentrations of 0.3 mM, 0.03 mmM, 0.003 mmM and 0.0003 mM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anticoagulated human blood using a one-step Ficoll-hypaque separation technique. (2) The mononuclear cells were washed three times in Hanks balanced salt solution (HBSS) with divalent cations and resuspended to a density of 2×10$^6$/ml in HBSS containing 1% BSA. Differential counts determined using the Abbott Cell Dyn 3500 analyzer indicated that monocytes ranged from 17 to 24% of the total cells in these preparations.

180 μl of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified CO$_2$ incubator, plates were removed and centrifuged (10 minutes at approximately 250×g) and the supernatants removed and assayed for TNFa using the R&D ELISA Kit.

Inhibition of Soluble TNF-α Production

The ability of the compounds or the pharmaceutically acceptable salts thereof to inhibit the cellular release of TNF-α and, consequently, demonstrate their effectiveness for treating diseases involving the disregulation of soluble TNF-α is shown by the following in vitro assay:

Method for the evaluation of recombinant TNF-α Converting Enzyme Activity Expression of recombinant TACE A DNA fragment coding for the signal sequence, preprodomain, prodomain and catalytic domain of TACE (amino acids 1–473), can be amplified by polymerase chain reaction using a human lung cDNA library as a template. The amplified fragment is then cloned into pFastBac vector. The DNA sequence of the insert is confirmed for both the strands. A bacmid prepared using pFastBac in E. coli DH10Bac is transfected into SF9 insect cells. The virus particles is then amplified to P1, P2, P3 stages. The P3 virus is infected into both Sf9 and High Five insect cells and grown at 27° C. for 48 hours. The medium is collected and used for assays and further purification.

Preparation of fluorescent quenched substrate:

A model peptidic TNF-α substrate (LY-LeucineAlanineGlutamineAlanineValine-ArginineSerine-SerineLysine(CTMR)-Arginine (LY=Lucifer Yellow; CTMR=Carboxytetramethyl-Rhodamine)) is prepared and the concentration estimated by absorbance at 560 nm ($E_{560}$, 60,000 M-1 CM-1) according to the method of Geoghegan, KF, "Improved method for converting an unmodified peptide to an energy-transfer substrate for a proteinase." *Bioconjugate Chem.* 7, 385–391 (1995). This peptide encompasses the cleavage cite on pro-TNF which is cleaved in vivo by TACE.

Expression of recombinant TACE

A DNA fragment coding for the signal sequence, preprodomain, prodomain and catalytic domain of TACE (amino acids 1–473), is amplified by polymerase chain reaction using a human lung cDNA library as a template. The amplified fragment is cloned into pFastBac vector. The DNA sequence of the insert is confirmed for both the strands. A bacmid prepared using pFastBac in E. coli DH10Bac is transfected into SF9 insect cells. The virus particles were amplified to P1, P2, P3 stages. The P3 virus is infected into both Sf9 and High Five insect cells and grown at 27° C. for 48 hours. The medium is collected and used for assays and further purification.

Enzyme reaction.

The reaction, carried out in a 96 well plate (Dynatech), is comprised of 70 μl of buffer solution (25 mM Hepes-HCl, pH7.5, plus 20 uM ZnCl$_2$), 10 μl of 100 μM fluorescent quenched substrate, 10 μl of a DMSO (5%) solution of test compound, and an amount of r-TACE enzyme which will cause 50% cleavage in 60 minutes—in a total volume of 100 μl. The specificity of the enzyme cleavage at the amide bond between alanine and valine is verified by HPLC and mass spectrometry. Initial rates of cleavage are monitored by measuring the rate of increase in fluorescence at 530 nm (excitation at 409 nm) over 30 minutes. The experiment is controlled as follows: 1) for background fluorescence of substrate; 2) for fluorescence of fully cleaved substrate; 3) for fluorescence quenching or augmentation from solutions containing test compound.

Data is analyzed as follows. The rates from the non-test compound containing "control" reactions were averaged to establish the 1 00% value. The rate of reaction in the presence of test compound was compared to that in the absence of compound, and tabulated as "percent of non-test compound containing control. The results are plotted as "% of control" vs. the log of compound concentration and a half-maximal point or $IC_{50}$ value determined.

All of the compounds of the invention have $IC_{50}$ of less than 1 μM, preferably less than 50 nM. Most preferred compounds of the invention are at least 100 fold less potent against r-MMP-1 than in the above TACE assay.

Human Monocyte Assay

Human mononuclear cells are isolated from anti-coagulated human blood using a one-step Ficoll-hypaque separation technique. (2) The mononuclear cells are washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180 m of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNF-α using the R&D ELISA Kit.

Aggrecanase Assay

Primary porcine chondrocytes from articular joint cartilage are isolated by sequential trypsin and collagenase digestion followed by collagenase digestion overnight and are plated at $2\times10^5$ cells per well into 48 well plates with 5 μCi/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM /1 % FBS overnight.

The following morning chondrocytes are washed once in DMEM/1%PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. |
| | Make a 100 uM stock of each compound in DMEM in 96 well plate. |
| | Store in freezer overnight. |
| | The next day perform serial dilutions in DMEM with IL-1 to 5 uM, 500 nM, and 50 nM. |
| | Aspirate final wash from wells and add 50 ul of compound from above dilutions to 450 ul of IL-1 media in appropriate wells of the 48 well plates. |
| | Final compound concentrations equal 500 nM, 50 nM, and 5 nM. |
| | All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

For administration to mammals, including humans, for the inhibition of matrix metalloproteinases or the production of tumor necrosis factor (TNF), a variety of conventional routes may be used including oral, parenteral (eg, intravenous, intramuscular or subcutaneous), buccal, anal and topical. In general, the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, eg., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

(2R, 4S)-4-(4-Methoxyphenyl)-5-oxopyrrolidine-2-carboxylic acid hydroxyamide

Step A: (5R)-3-Bromo-5-(tert-butyl-dimethylsilanyloxymethyl)-2-oxo-2,5-dihydropyrrole-1-carboxylic acid tert-butyl ester A solution of 2-(tert-butyldimethylsilanyloxymethyl)-5-oxopyrrolidine-1-carboxylic acid tert-butyl ester (16.5 grams, 50 mmol) in tetrahydrofuran (800 mL) was cooled in bath at −78° C. A 1M solution of lithium bis(trimethylsilyl) amide in tetrahydrofuran (100 mL, 100 mmol) was added slowly. After stirring for 2 hours, a solution of phenylselenylbromide (14.16 grams, 60 mmol) in tetrahydrofuran (100 mL) was added and, after 15 minutes, a solution of 1,2-dibromotetrachloroethane (19.5 grams, 60 mmol) in tetrahydrofuran (100 mL) was added. The reaction mixture was stirred for an additional 1.5 hours while cooling at −78° and was quenched by addition of saturated ammonium chloride solution. Water and diethyl ether were added. The aqueous phase was separated and extracted with diethyl ether. The combined organic layers were concentrated to an orange oil which was dissolved in methylene chloride (1000 mL). A 30% w/v aqueous solution of hydrogen peroxide (20 mL) was added and the mixture was stirred vigorously overnight. Water (50 mL) was added. The aqueous layer was separated and extracted with methylene chloride. The combined organic layers were dried over magnesium sulfate and concentrated to an orange oil. The title compound (12.0 grams, 59%) was isolated by flash chromatography on silica gel eluting first with a 1:1 mixture of hexane and methylene chloride and then with methylene chloride alone.

$^1$H NMR (CDCl$_3$): $\delta$7.31 (d, J=2.3 Hz, 1 H), 4.56–4.53 (m, 1 H), 4.08 (dd, J=3.4, 10.0 Hz, 1 H), 3.74 (dd, J=6.2, 10.0 Hz, 1 H), 1.53 (s, 9 H), 0.83 (s, 9 H), 0.01 (s, 3 H), 0.00 (s, 3 H).

$^{13}$C NMR (CDCl$_3$): $\delta$164.0, 149.1, 146.3, 118.2, 83.6, 62.8, 61.8, 28.0, 25.6, 18.0, −5.6, −5.7.

Step B: (5R)-5-(tert-Butyl-dimethylsilanyloxymethyl)-3-(4-methoxyphenyl)-2-oxo-2,5-dihydropyrrole-1-carboxylic acid tert-butyl ester The diethanolamine complex of 4-methoxyphenyl boronic acid (2.5 grams, 11 mmol) was stirred in a mixture of diisopropyl ether (50 mL) and 1.5M aqueous hydrochloric acid solution (30 mL) for 2 hours. After separation of the aqueous layer, toluene (50 mL) was added and the mixture was concentrated to remove most of the diisopropyl ether. (5R)-3-Bromo-5-(tert-butyl-dimethylsilanyloxymethyl)-2-oxo-2,5-dihydropyrrole-1 -carboxylic acid tert-butyl ester (3.0 grams, 7.38 mmol), toluene (150 mL), and a solution of sodium carbonate (850 mg, 8 mmole) in water (20 mL) were added. After purging the solution of oxygen, tetrakis (triphenylphosphene)palladium (0) (250 mg) was added and the mixture was heated at reflux for 2.5 hours. The mixture was cooled and diluted with toluene and water. The organic layer was separated, washed with brine, dried over magnesium sulfate and concentrated to a brown oil. The title compound (1.7 grams, 53%), was isolated by flash chromatography on silica gel eluting with methylene chloride.

$^1$H NMR (CDCl$_3$): $\delta$7.74 (d, J=8.9 Hz, 2 H), 7.24 (d, J=2.5 Hz, 1 H), 6.88 (d, J=8.9 Hz, 2 H), 4.57–4.54 (m, 1 H), 4.17 (dd, J=3.6, 9.6 Hz, I H), 3.79 (s, 3 H), 3.72 (dd, J=6.6, 9.6Hz, 1 H), 1.55 (s, 9 H), 0.82 (s, 9 H), 0.02 (s, 3 H), 0.01 (s, 3 H).

Step C: (3S , 5R)-5-Hydroxymethyl-3-(4-methoxyphenyl)-2-oxopyrrolidine-1-carboxylic acid tert-butyl ester A solution of (5R)-5-(tert-butyl-dimethylsilanyloxymethyl)-3-(4-methoxyphenyl)-2-oxo-2,5-dihydropyrrole-1-carboxylic acid tert-butyl ester (1.7 grams, 3.9 mmol) in ethanol (100 mL) was treated with palladium black (300 mg) and hydrogenated in a Parr™ shaker at 3 atmospheres pressure overnight. The catalyst was removed by filtration and the solvent was evaporated to provide crude (3S, 5R)-5-(tert-butyl-dimethylsilanyloxymethyl)-3-(4-methoxyphenyl)-2-oxopyrrolidine-1-carboxylic acid tert-butyl ester as an oil. This was dissolved in tetrahydrofuran (40 mL) and treated with aqueous 0.5M hydrochloric acid solution (7.2 mL). The resulting mixture was stirred at room temperature overnight, quenched with saturated sodium carbonate solution and extracted twice with methylene chloride. The combined organic extracts were dried over magnesium sulfate and concentrated to an oil. The title compound (551 mg, 48%)

was isolated by flash chromatography on silica gel eluting with 20% hexane in ethyl acetate.

$^1$H NMR (CDCl$_3$): δ7.15 (d, J=8.7 Hz, 2 H), 6.84 (d, J=8.7 Hz, 2 H), 4.18–4.13 (m, 1 H), 3.81–3.65 (m, 4 H), 3.76 (s, 3 H, overlapped), 2.58–2.51 (m, 1 H), 1.96–1.87 (m, 1 H), 1.52 (s, 9 H).

Step D: (2R, 4S)-4-(4-Methoxyphenyl)-5-oxopyrrolidine-1,2-dicarboxylic acid 1-tert-butyl ester A stock solution containing 12.0 grams of periodic acid and chromium trioxide (24 mg) in wet acetonitrile (0.75 volume % water) was prepared. A portion of this solution (9.6 mL) was added to a solution of (3S, 5R)-5-hydroxymethyl-3-(4-methoxyphenyl)-2-oxopyrrolidine-1-carboxylic acid tert-butyl ester (510 mg, 1.58 mmol) in wet acetonitrile (0.75 volume % water) at 0° C. The reaction mixture was stirred at 0° C. for 2 hours and then quenched by addition of a solution of dibasic sodium phosphate (1.2 grams) in water (20 mL). The mixture was extracted with ethyl acetate and the organic extract was washed with aqueous sodium bisulfite solution and brine. After drying over magnesium sulfate, the solvent was evaporated to provide the title compound as a white solid, 518 mg (98%).

$^1$H NMR (CDCl$_3$): δ8.56 (br s, 1 H), 7.13 (d, J=8.6 Hz, 2 H), 6.82 (d, J=8.6 Hz, 2 H), 4.58 (apparent t, J=8.3 Hz, 1 H), 3.78–3.73 (m, 1 H), 3.73 (s, 3 H), 2.86–2.79 (m, 1 H), 2.13–2.05 (m, 1 H), 1.45 (s, 9 H).

$^{13}$C NMR (CDCl$_3$): δ176.2, 173.2, 159.0, 149.4, 129.2, 129.0, 114.2, 84.3, 56.8, 55.2, 47.9, 30.2, 27.8.

MS m/z 334 (M-1), 234.

[α]$_D$=+4.4°(c=1.12, CHCl$_3$).

Step E: (3S, 5R)-5-benzyloxycarbamoyl-3-(4-methoxyphenyl)-2-oxopyrrolidine-1-carboxylic acid tert-butyl ester To a solution of (2R, 4S)-4-(4-methoxyphenyl)-5-oxopyrrolidine-1,2-dicarboxylic acid 1-tert-butyl ester (305 mg, 0.91 mmol), diisopropylethylamine (0.35 mL, 2.0 mmol) and O-benzylhydroxylamine hydrochloride (160 mg, 1.0 mmol) in methylene chloride (20 mL) was added (benztriazol-1-yloxy)tris(dimethylamino)phosphonium hexafluoroborate (443 mg, 1.0 mmol). The reaction was stirred at room temperature overnight. After dilution with methylene chloride, the mixture was washed with aqueous saturated sodium bicarbonate solution, water and brine. The solution was dried over magnesium sulfate and concentrated to a white solid from which the title compound (294 mg, 73%) was isolated by flash chromatography eluting with 25% hexane in ethyl acetate.

MS m/z 439 (M-1), 339.

Step F: (2R, 4S)-4-(4-Methoxyphenyl)-5-oxopyrrolidine-2-carboxylic acid benzyloxyamide Hydrogen chloride gas was bubbled for 3 minutes through a solution of (3S, 5R)-5-benzyloxycarbamoyl-3-(4-methoxyphenyl)-2-oxopyrrolidine-1-carboxylic acid tert-butyl ester (270 mg, 0.61 mmol) in methylene chloride (40 mL). After stirring for an additional 10 minutes, the solvent was evaporated to leave a white foam. The title compound (169 mg, 80%) was isolated by flash chromatography (eluting with ethyl acetate) and recrystallization from a mixture of ethyl acetate and hexane.

$^1$H NMR (CDCl$_3$): δ10.40 (br s, 1 H), 7.30–7.23 (m, 5 H), 7.15 (br s, 1 H), 7.04 (d, J=8.5 Hz, 2 H), 6.76 (d, J=8.5 Hz, 2 H), 4.79–4.72 (m, 2 H), 3.89 (apparent t, J=7.3 Hz, 1 H), 3.70 (s, 3 H), 3.45 (apparent t, J=9.6 Hz, I H), 2.77–2.69 (m, 1 H), 2.06–1.98 (m, 1 H).

$^{13}$C NMR (CDCl$_3$): δ179.1, 169.3, 158.8, 134.9, 130.0, 129.3, 129.2, 128.7, 128.5, 114.2, 78.1, 55.2, 53.9, 46.6, 34.6.

MS m/z 341 (M+1).

[α]$_D$=+39.9° (c=0.91, CHCl$_3$).

(2R, 4S)4-(4-Methoxyphenyl)-5-oxopyrrolidine-2-carboxylic acid hydroxyamide

A solution of (2R, 4S)-4-(4-methoxyphenyl)-5-oxopyrrolidine-2-carboxylic acid benzyloxyamide (150 mg, 0.44 mmol) in methanol (15 mL) was treated with 5% palladium on barium sulfate (40 mg) and hydrogenated in a Parr™ shaker at 3 atmospheres pressure for 2.5 hours. The catalyst was removed by filtration and the solvent was evaporated to provide a solid. The title compound (106 mg, 96%) was isolated by crystallization from a mixture of ethyl acetate and hexane.

$^1$H NMR (DMSO-d$_6$): δ10.77 (br s, 1 H), 8.97 (br s, 1 H), 8.01 (br s, 1 H), 7.14 (d, J=8.4 Hz, 2 H), 6.84 (d, J=8.4 Hz, 2 H), 3.91 (apparent t, J=7.8 Hz, 1 H), 3.69 (s, 3 H), 3.53 (apparent t, J=7.8 Hz, 1 H), 2.67–2.58 (m, 1 H), 1.92–1.84 (m, 1 H).

MS m/z 249 (M-1).

EXAMPLE 2

(2R, 4S)4-[4-(4-Fluorophenoxy)phenyl]-5-oxo-pyrrolidine-2-carboxylic acid hydroxyamide Prepared according to the method of Example 1 starting with the diethanolamine complex of 4-(4-fluorophenoxy) phenyl boronic acid.

$^1$H NMR (DMSO-d$_6$): δ10.78 (br s, 1 H), 8.98 (br s, 1 H), 8.06 (s, 1 H), 7.23 (d, J=8.7 Hz, 2H), 7.19–7.15 (m, 2 H), 7.02–6.98 (m, 2 H), 6.89 (d, J=8.7 Hz, 2 H), 3.91 (apparent t, J=7.8 Hz, 1 H), 3.59 (apparent t, J=9.8 Hz, 1 H), 2.67–2.60 (m, 1 H), 1.94–1.86 (m, 1 H).

$^{13}$C NMR (DMSO-d$_6$): δ176.0, 167.8, 157.6 (d, J=240 Hz), 155.2, 152.3, 134.8, 129.4, 119.9 (d, J=9 Hz), 117.5, 116.0 (d, J=23 Hz), 51.4, 45.5, 33.6.

MS m/z 329 (M-1).

[α]$_D$=+24.30 (c =1.14, MeOH).

EXAMPLE 3

(2R, 4S)-4-(4'-Fluorobiphenyl4-yl)-5-oxo-pyrrolidine-2-carboxylic acid hydroxyamide Prepared according to the method of Example 1 starting with the diethanolamine complex of 4'-fluorobiphen-4-yl boronic acid. Recrystallized from methanol, mp: 193–202° C.

$^1$H NMR (DMSO-d$_6$): δ10.77 (br s, 1 H), 8.97 (br s, 1 H), 8.08 (s, 1 H), 7.67–7.63 (m, 2 H), 7.55 (d, J=8.1 Hz, 2 H), 7.32 (d, J=8.1 Hz, 2 H), 7.24 (apparent t, J=8.8 Hz, 2 H), 3.95 (apparent t, J=7.8 Hz, 1 H), 3.65 (apparent t, J=9.7 Hz, 1 H), 2.71–2.64 (m, 1 H), 2.00–1.93 (m, 1 H).

MS: m/z 313 (M-1).

Analysis calculated for C$_{17}$H$_{15}$FN$_2$O$_3$.½H$_2$0: C, 63.15; H, 4.99; N, 8.66. Found: C, 62.83; H, 5.48; N, 8.39.

EXAMPLE 4

(2R, 4S )-4-[3-(4-Fluorophenoxy)phenyl]-5-oxo-pyrrolidine-2-carboxylic acid hydroxyamide Prepared according to the method of Example 1 starting with the diethanolamine complex of 3-(4-fluorophenoxy) phenyl boronic acid. Recrystallized from ethyl acetate, mp: 151–152° C.

$^1$H NMR (DMSO-d$_6$): δ10.79 (s, 1 H), 8.98 (s, 1 H), 8.08 (s, 1 H), 7.28 (apparent t, J =7.9 Hz, 1 H), 7.22–7.18 (m, 2

H), 7.04–7.01 (m, 3 H), 6.93 (apparent s, 1 H), 6.78 (dd, J=2.5, 8.3 Hz, 1 H), 3.91 (apparent t, J=7.6 Hz, 1 H), 3.62 (apparent t, J=9.8 Hz, 1 H), 2.69–2.62 (m, 1 H), 1.95–1.87 (m, 1 H).

MS: m/z329 (M−1).

$[\alpha]_D$=+17.9° (c=1.00, MeOH)

Analysis calculated for $C_{17}H_{15}FN_2O_4$: C, 61.82; H, 4.58; N, 8.48. Found: C, 61.85; H, 4.59; N, 8.40.

EXAMPLE 5

(2R, 4S)-4-Naphthalen-2-yl-5-oxo-pyrrolidine-2-carboxylic acid hydroxyamide

Prepared according to the method of Example 1 starting with 2-naphthyl boronic acid. Recrystallized from ethyl acetate/methanol, mp: 197–199° C.

$^1$H NMR (DMSO-d$_6$): δ10.82 (br s, 1 H), 9.00 (s, 1 H), 8.14 (s, 1 H), 7.86–7.83 (m, 3 H), 7.75 (apparent s, 1 H), 7.46–7.42 (m, 3 H), 4.00 (apparent t, J=7.6 Hz, 1 H), 3.80 (apparent t, J=9.6 Hz, 1 H), 2.77–2.72 (m, 1 H), 2.10–2.03 (m, 1 H).

MS: m/z 269 (M−1).

$[\alpha]_D$=0° (c=0.33, MeOH)

Analysis calculated for $C_{15}H_{14}N_2O_3$: C, 66.66; H, 5.22; N, 10.36. Found: C, 66.43; H, 5.41; N, 10.10.

EXAMPLE 6

(2R, 4S)-5-Oxo-4-(4-phenethylphenyl)-pyrrolidine-2-carboxylic acid hydroxyamide

Prepared according to the method of Example 1 starting with 4-styrylphenyl boronic acid. (The styryl double bond is reduced to a phenethylphenyl group at the same time the 2-oxo-2,5-dihydropyrrole double bond is hydrogenated.)

$^1$H NMR (DMSO-d$_6$): δ10.78 (br s, 1 H), 8.97 (s, 1 H), 8.03 (s, 1 H), 7.24–7.22 (m, 4 H), 7.14 (apparent s, 5 H), 3.92 (apparent t, J=7.4 Hz, 1 H), 3.55 (apparent t, J=9.9 Hz, 1 H), 2.82 (apparent s, 4 H), 2.67–2.60 (m, 1 H), 1.95–1.87 (m, 1 H).

MS: m/z=325 (M+1).

EXAMPLE 7

(2R, 4S)-4-(4-Benzyloxyphenyl)-5-oxo-pyrrolidine-2-carboxylic acid hydroxyamide

Step A: (5R)-3-(4-Benzyloxyphenyl)-5-(tert-butyidimethylsilanyloxymethyl)-2-oxo-2,5-dihydro-pyrrole-1-carboxylic acid tert-butyl ester The diethanolamine complex of 4-phenethylphenyl boronic acid (8.25 g, 27.8 mmol) was stirred in a mixture of diethyl ether (165 mL) and 3M aqueous HCl solution (66 mL) for 3 hours. After separation of the aqueous layer, toluene (100 mL) was added and the mixture was concentrated to remove most of the diethyl ether. (5R)-3-Bromo-5-(tert-butyl-dimethylsilanyloxymethyl)-2-oxo-2,5-dihydropyrrole-1-carboxylic acid tert-butyl ester (7.5 g, 18.5 mmol) and a solution of $Na_2CO_3$ (1.25 g, 11.8 mmole) in water (25 mL) were added. After purging the solution of oxygen, tetrakis(triphenylphosphene)palladium (0) (424 mg) was added and the mixture was heated at reflux for 18 h. The mixture was cooled and diluted with toluene and water. The organic layer was separated, washed with brine, dried over $MgSO_4$ and concentrated to a dark oil. The title compound (5.5 g, 58%), was isolated as a pale yellow solid by flash chromatography on silica gel eluting 15% diethyl ether in hexane.

Step B: (3S,5R)-3-(4-Benzyloxyphenyl)-5-(tert-butyidimethylsilanyloxymethyl)-2-oxo-pyrrolidine-1-carboxylic acid tert-butyl ester A solution of (5R)-3-(4-benzyloxyphenyl)-5-(tert-butyldimethylsilanyloxymethyl)-2-oxo-2,5-dihydro-pyrrole-1-carboxylic acid tert-butyl ester (2.0 g, 3.92 mmol) in ethyl acetate (40 mL) and hexane (40 mL) was treated with 20% palladium hydroxide on carbon (200 mg) and hydrogenated in a Parr™ shaker at 3 atmospheres pressure for 2 hours. The catalyst was removed by filtration and the solvent was evaporated to provide the title compound as a yellow oil (2.0 g, 100%).

Step C: (3S,5R)-3-(4-Benzyloxyphenyl)-5-hydroxymethyl-2-oxo-pyrrolidine-1-carboxylic acid tert-butyl ester A solution of (3S,5R)-3-(4-benzyloxyphenyl)-5-(tert-butyldimethylsilanyloxymethyl)-2-oxo-pyrrolidine-1-carboxylic acid tert-butyl ester (2.0 g, 3.91 mmol) in tetrahydrofuran (45 mL) was cooled in an ice bath. Aqueous 0.5M HCl solution (7.8 mL, 3.9 mmol) was added and the resulting mixture was allowed to warm to room temperature while stirring overnight. After a total reaction time of 24 hours, saturated aqueous $NaHCO_3$ solution was added. The mixture was extracted twice with diethyl ether and the combined organic phases were washed with brine, dried over $MgSO_4$ and concentrated to an oil. The title compound, a colorless oil (1.02 g, 65%), was isolated by flash chromatography on silica gel eluting with 50% ethyl acetate in hexane.

Step D: (2R, 4S)-4-(4-Benzyloxyphenyl)-5-oxo-pyrrolidine-2-carboxylic acid

A solution containing 6.0 g of periodic acid and chromium trioxide (13 mg) in wet acetonitrile (60 mL; 0.75 volume % water) was prepared. A portion of this solution (15 mL) was added dropwise to a solution of (3S,5R)-3-(4-benzyloxyphenyl)-5-hydroxymethyl-2-oxo-pyrrolidine-1-carboxylic acid tert-butyl ester (1.02 g, 2.57 mmol) in wet acetonitrile (15 mL; 0.75 volume % water) at 0° C. The reaction mixture was stirred at 0° C. for 2 hours. At this time, more of the periodic acid/chromium trioxide solution (5 mL) was added. Stirring at 0° C. was continued for an additional 1 hour. After quenching with a solution of dibasic sodium phosphate (720 mg) in water (12 mL), the mixture was extracted twice with diethyl ether. The combined organic extracts were washed with aqueous sodium bisulfite solution (440 mg in 10 mL water) and brine. After drying over $MgSO_4$, the solvent was evaporated to provide a yellow solid that was taken up in methylene chloride (100 mL) and cooled in an ice bath. Hydrogen chloride gas was bubbled through the cold solution for 2 minutes and the resulting mixture was stirred at 0° C. for 1 hour. The solvent and HCl were evaporated to afford a solid from which the title compound, 226 mg (28%) was isolated by trituration with a mixture of methylene chloride, diethyl ether and ethyl acetate. The trituration filtrate was dissolved in aqueous saturated $NaHCO_3$ solution and washed twice with diethyl ether. After careful acidification with aqueous 6M HCl solution, the aqueous layer was extracted twice with ethyl acetate. The combined organic layers were washed with brine, dried over $MgSO_4$ and concentrated to provide more of the title compound, 123 mg (15%).

Step E: (2R, 4S)-4-(4-Benzyloxyphenyl)-5-oxo-pyrrolidine-2-carboxylic acid (2-trimethylsilanylethoxy) amide To a solution of (2R, 4S)-4-(4-benzyloxyphenyl)-5-oxo-pyrrolidine-2-carboxylic acid (330 mg, 1.06 mmol), N-methyl morpholine (0.25 mL, 2.3 mmol) and O-(2-trimethylsilylethyl) hydroxylamine hydrochloride (220 mg, 1.30 mmol) in $CH_2Cl_2$ (20 mL) was added (benztriazol-1-yloxy)tris(dimethylamino)phosphonium hexafluoroborate (560 mg, 1.27 mmol). The reaction was stirred at room temperature for 6 hours. After dilution with $CH_2Cl_2$, the mixture was washed sequentially with aqueous 0.5M HCl solution, water, aqueous saturated $NaHCO_3$ solution, and brine. The solution was dried over MgSO4 and concentrated to a white solid that was triturated with ethyl acetate and set aside. The trituration filtrate was concentrated and chromatographed on silica gel eluting with 5% methanol in chloroform. Fractions containing the title compound were combined and concentrated to afford a white solid that was combined with the solid obtained directly from the crude product mixture. The sample was stirred in water overnight. The title compound was collected by filtration and dried. The yield was 194 mg (43%).

Step F: (2R, 4S )-4-(4-Benzyloxyphenyl)-5-oxo-pyrrolidine-2-carboxylic acid hydroxyamide To a suspension of (2R, 4S)-4-(4-benzyloxyphenyl)-5-oxo-pyrrolidine-2-carboxylic acid (2-trimethylsilanylethoxy)amide (95 mg, 0.22 mmol) in methylene chloride was added boron trifluoride etherate (0.86 μL, 0.68 mmol). The mixture was stirred at room temperature for 75 minutes. During this period the suspended solid dissolved completely and the product precipitated. The mixture was quenched by addition of saturated aqueous $NH_4Cl$ solution. The title compound was collected by filtration, washing well with ethyl acetate and water, and dried. The yield was 56 mg (78%).

$^1H$ NMR (DMSO-$d_6$): δ10.74 ( br s, 1 H), 8.95 (br s, 1 H), 8.00 (br s, 1 H), 7.70–7.27 (m, 5 H), 7.13 (d, J=8.0 Hz, 2 H), 6.91 (d, J=8.0 Hz, 2 H), 5.04 (apparent s, 2 H), 3.89 (apparent t, J=7.7 Hz, 1 H), 3.51 (apparent t, J=9.7 Hz, 1 H), 2.64–2.57 (m, 1 H), 1.91–1.83 (m, 1 H).

MS: m/z 325 (M−1).

What is claimed is:

1. A compound of the formula

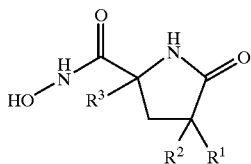

wherein $R^1$ is $(C_1-C_6)$alkyl, $(C_6-C_{10})$aryl, $(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroayloxy$(C_2-C_9)$heteroaryl, $(C_6-C_{10})$aryl$(C_1-C_6)$alkyl$(C_6-C_{10})$aryl, $(C_6-C_{10})$aryl$(C_1-C_6)$alkyl$(C_2-C_9)$heteroaryl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_6-C_{10})$aryloxy$(C_1-C_6)$alkyl$(C_6-C_{10})$aryl, $(C_6-C_{10})$aryloxy$(C_1-C_6)$alkyl$(C_2-C_9)$heteroaryl, $(C_2-C_9)$heteroaryl$(C_1-C_6)$alkyl$(C_6-C_{10})$aryl, $(C_2-C_9)$heteroaryl$(C_1-C_6)$alkyl$(C_2-C_9)$heteroaryl, $(C_2-C_9)$heteroaryl$(C_1-C_6)$alkoxy$(C_6-C_{10})$aryl, $(C_2-C_9)$heteroaryl$(C_1-C_6)$alkoxy$(C_2-C_9)$heteroaryl, $(C_2-C_9)$heteroaryloxy$(C_1-C_6)$alkyl$(C_6-C_{10})$aryl, $(C_2-C_9)$heteroaryloxy$(C_1-C_6)$alkyl$(C_2-C_9)$heteroaryl, $(C_6-C_{10})$aryl$(C_6-C_{10})$aryl$(C_1-C_6)$alkyl or $(C_6-C_{10})$aryl$(C_1-C_6)$alkoxy$(C_1-C_6)$alkyl, wherein each of said $(C_6-C_{10})$aryl or $(C_2-C_9)$heteroaryl moieties is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy; and $R^2$ and $R^3$ are independently selected from H, $(C_1-C_6)$ alkyl, and $CH_2(C_6-C_{10})$aryl;

or a pharmaceutically acceptable salt thereof.

2. A compound according to claim 1 wherein $R^1$ is $(C_6-C_{10})$aryl, $(C_6-C_{10})$aryloxy$(C_6-C_{10})$aryl, $(C_6-C_{10})$aryl$(C_6-C_{10})$aryl, $(C_6-C_{10})$aryloxy$(C_2-C_9)$heteroaryl, $(C_2-C_9)$heteroaryl, $(C_2-C_9)$heteroaryl$(C_2-C_9)$heteroaryl, $(C_6-C_{10})$aryl$(C_1-C_6)$alkoxy$(C_6-C_{10})$aryl, $(C_2-C_9)$heteroaryloxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_2-C_9)$heteroaryl, $(C_6-C_{10})$aryl$(C_2-C_9)$heteroaryl, $(C_2-C_9)$heteroaryl$(C_6-C_{10})$aryl, $(C_2-C_9)$heteroaryl$(C_1-C_6)$alkoxy$(C_6-C_{10})$aryl, or $(C_2-C_9)$heteroaryl$(C_1-C_6)$alkoxy$(C_2-C_9)$heteroaryl, wherein each $(C_6-C_{10})$aryl or $(C_2-C_9)$heteroaryl moieties of said $(C_6-C_{10})$aryl, $(C_6-C_{10})$aryloxy$(C_6-C_{10})$aryl, $(C_6-C_{10})$aryl$(C_6-C_{10})$aryl, $(C_6-C_{10})$aryloxy$(C_2-C_9)$heteroaryl, $(C_2-C_9)$heteroaryl, $(C_6-C_{10})$aryl$(C_1-C_6)$alkoxy$(C_6-C_{10})$aryl, $(C_2-C_9)$heteroaryloxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_2-C_9)$heteroaryl, $(C_6-C_{10})$aryl$(C_2-C_9)$heteroaryl, $(C_2-C_9)$heteroaryl$(C_6-C_{10})$aryl, $(C_2-C_9)$heteroaryl$(C_1-C_6)$alkoxy$(C_6-C_{10})$aryl, or $(C_2-C_9)$heteroaryl$(C_1-C_6)$alkoxy$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy.

3. A compound according to claim 1 with the stereochemistry

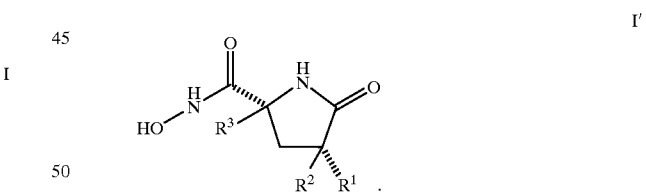

4. A compound according to claim 3, wherein $R^1$ is optionally substituted $(C_6-C_{10})$aryl.

5. A compound according to claim 3, wherein $R^1$ is optionally substituted $(C_6-C_{10})$aryloxy$(C_6-C_{10})$aryl.

6. A compound according to claim 3, wherein $R^1$ is optionally substituted $(C_2-C_9)$heteroaryloxy$(C_6-C_{10})$aryl.

7. A compound according to claim 3, wherein $R^1$ is optionally substituted $(C_6-C_{10})$aryl$(C_1-C_6)$alkoxy$(C_6-C_{10})$aryl.

8. A compound according to claim 3, wherein said $R^1$ optional substituent is hydrogen, fluoro, chloro, $(C_1-C_6)$ alkyl or $(C_1-C_6)$alkoxy.

9. A compound according to claim 3, wherein said $R^1$ optional substituent is in the para position of the terminal ring.

10. A compound according to claim 3, wherein said $R^1$ optional substituent is in the ortho position of the terminal ring.

11. A compound according to claim 3 wherein $R^2$ and $R^3$ are hydrogen.

12. A compound according to claim 3 wherein one or both of $R^2$ and $R^3$ are independently selected from $(C_1–C_6)$alkyl, and $CH_2(C_6–C_{10})$aryl.

13. A compound according to claim 3, wherein said compound is selected from the group consisting of:

(2R,4S)-4-(4-methoxyphenyl)-5-oxopyrrolidine-2-carboxylic acid hydroxyamide;

(2R,4S)-4-[4-(4-fluorophenoxy)phenyl]-5-oxopyrrolidine-2-carboxylic acid hydroxyamide;

(2R,4S)-5-oxo-4-(4-phenoxyphenyl)-pyrrolidine-2-carboxylic acid hydroxyamide;

(2R,4S)-4-[4-(4-chlorophenoxy)phenyl]-5-oxopyrrolidine-2-carboxylic acid hydroxyamide;

(2R,4S)-4-[3-(4-chlorophenoxy)phenyl]-5-oxopyrrolidine-2-carboxylic acid hydroxyamide;

(2R,4S)-4-[3-(4-fluorophenoxy)phenyl]-5-oxopyrrolidine-2-carboxylic acid hydroxyamide;

(2R,4S)-5-oxo-4-[4-(pyridin-4-yloxy)-phenyl]pyrrolidine-2-carboxylic acid hydroxyamide;

(2R,4S)-4-biphenyl-4-yl-5-oxo-pyrrolidine-2-carboxylic acid hydroxyamide;

(2R,4S)-4-(4'-fluorobiphenyl-4-yl)-5-oxopyrrolidine-2-carboxylic acid hydroxyamide;

(2R,4S)-4-(4-benzyloxyphenyl)-5-oxopyrrolidine-2-carboxylic acid hydroxyamide;

(2R,4S )-5-oxo-4-(4-phenethylphenyl)-pyrrolidine-2-carboxylic acid hydroxyamide;

(2R,4S)-4-[4-(4-fluorobenzyloxy)phenyl]-5-oxopyrrolidine-2-carboxylic acid hydroxyamide;

(2R,4S)-4-[4-(3,5-difluorobenzyloxy)phenyl]-5-oxopyrrolidine-2-carboxylic acid hydroxyamide;

(2R,4S)-4-(4-methoxybenzyl)-5-oxopyrrolidine-2-carboxylic acid hydroxyamide;

(2R,4S)-4-(4'-fluorobiphenyl-4-ylmethyl)-5-oxopyrrolidine-2-carboxylic acid hydroxyamide;

(2R, 4S )-4-naphthalen-2-yl-5-oxo-pyrrolidine-2-carboxylic acid hydroxyamide;

(2R, 4S)-4-[4-(4-fluorophenoxy)-phenyl]-2,4-dimethyl-5-oxo-pyrrolidine-2-carboxylic acid hydroxyamide;

(2R, 4S)-4-[4-(4-fluorophenoxy)-phenyl]-4-methyl-5-oxo-pyrrolidine-2-carboxylic acid hydroxyamide;

(2R, 4R)-4-benzyl-5-oxo-4-(4-phenoxyphenyl)-pyrrolidine-2-carboxylic acid hydroxyamide;

(2R, 4S)-4-[4-(4-chlorophenoxy)phenyl]-4-methyl-5-oxo-pyrrolidine-2-carboxylic acid hydroxyamide; and (2R, 4S)-4-[4-(4-chlorophenoxy)phenyl]-2,4-dimethyl-5-oxo-pyrrolidine-2-carboxylic acid hydroxyamide.

14. A pharmaceutical composition for the treatment of a condition selected from the group consisting of arthritis inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, comprising an amount of a compound of claim 1 effective in such treatment and a pharmaceutically acceptable carrier.

15. A method for treating a condition selected from the group consisting of arthritis inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis aortic aneurysm, congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, comprising administering to said mammal an amount of a compound of claim 1, effective in treating such a condition.

16. A pharmaceutical composition for the treatment of a condition which can be treated by the inhibition of matrix metalloproteinases in a mammal, comprising an amount of a compound of claim 1 effective in such treatment and a pharmaceutically acceptable carrier.

17. A pharmaceutical composition for the treatment of a condition which can be treated by the inhibition of a mammalian reprolysin in a mammal, comprising an amount of a compound of claim 1 effective in such treatment and a pharmaceutically acceptable carrier.

18. A method for the inhibition of matrix metalloproteinases in a mammal, comprising administering to said mammal an effective amount of a compound of claim 1.

19. A method for the inhibition of a mammalian reprolysin in a mammal, comprising administering to said mammal an effective amount of a compound of claim 1.

* * * * *